United States Patent [19]

Sutton et al.

[11] Patent Number: 5,401,633
[45] Date of Patent: Mar. 28, 1995

[54] BIOLOGICALLY ACTIVE REAGENT PREPARED FROM ALDEHYDE-CONTAINING POLYMER, TEST KIT, ANALYTICAL ELEMENT AND METHODS OF USE

[75] Inventors: Richard C. Sutton, Rochester; Ignazio S. Ponticello, Pittsford; Susan J. Danielson, Rochester, all of N.Y.

[73] Assignee: Eastman Kodak Company, Rochester, N.Y.

[21] Appl. No.: 955,167

[22] Filed: Oct. 1, 1992

[51] Int. Cl.6 .......................................... G01N 33/546
[52] U.S. Cl. ........................................ 435/6; 435/7.93; 435/7.94; 436/501; 436/533; 436/534; 530/413
[58] Field of Search ...................... 436/533, 534, 501; 435/6, 7.93; 422/56, 57; 427/3; 428/407; 530/413

[56] References Cited

U.S. PATENT DOCUMENTS

| | | | |
|---|---|---|---|
| 3,847,743 | 11/1974 | Forgione | 195/63 |
| 4,017,364 | 4/1977 | Van Leemputten | 195/68 |
| 4,225,689 | 9/1980 | Wilson | 526/75 |
| 4,401,765 | 8/1983 | Craig et al. | 436/533 |
| 4,413,070 | 11/1983 | Rembaum | 435/180 |
| 4,438,239 | 3/1984 | Rembaum et al. | 526/315 |
| 4,480,042 | 10/1984 | Craig et al. | 436/533 |
| 4,552,633 | 11/1985 | Kumakura et al. | 435/180 |
| 4,563,431 | 1/1986 | Pauly et al. | 436/533 |
| 4,732,811 | 3/1988 | Margel | 428/403 |

FOREIGN PATENT DOCUMENTS 134660 3/1985 European Pat. Off. .
350407 1/1990 European Pat. Off. .
2663337 12/1991 France .

OTHER PUBLICATIONS

J. Kalal et al., Chemical Abstracts, vol. 91, No. 922485 (1979), Abstract of Canadian Patent No. 1,054,743 (15 May 1979).

*Primary Examiner*—Mary E. Ceperley
*Attorney, Agent, or Firm*—James L. Tucker

[57] ABSTRACT

A biologically active reagent is prepared by reacting a biologically active substance covalently to a polymeric particle having pendant aldehyde groups. Such groups are provided by a polymerizable monomer represented by the structure:

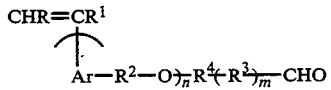

wherein Ar is arylene, R and $R^1$ are independently hydrogen, halo or lower alkyl, $R^2$ and $R^3$ are independently alkylene of 1 to 4 carbon atoms in the chain, $R^4$ is arylene, m is 0 or 1, and n is an integer of 1 to 4. These reagents can be used in a variety of specific binding and affinity purification methods, and in both solution assays and dry analytical elements.

29 Claims, No Drawings

BIOLOGICALLY ACTIVE REAGENT PREPARED FROM ALDEHYDE-CONTAINING POLYMER, TEST KIT, ANALYTICAL ELEMENT AND METHODS OF USE

FIELD OF THE INVENTION

The present invention relates to biologically active reagents prepared using polymeric particles. It also relates to test kits and analytical elements containing same, and to immunoassays and specific binding assays using such reagents. Further, it relates to an analytical purification method using the reagents. This invention can be used for various clinical, diagnostic, medical and research purposes.

BACKGROUND OF THE INVENTION

There is a continuing need in medical practice and research, and in analytical and diagnostic procedures for rapid and accurate determinations of chemical and biological substances which are present in various fluids, such as biological fluids. For example, the presence of drugs, hormones, steroids, polypeptides, metabolites, toxins, viruses, microorganisms or nucleic acids in human or animal body fluids or tissues must be determined rapidly and accurately for effective research, diagnosis or treatment.

In approximately the last twenty years, a wide variety of analytical methods have been developed to detect the substances noted above. Generally, the state of the art has advanced to such a degree that analytical and diagnostic methods have become highly reliable and suitable for automation or for use with test kits which can be readily used in doctors' offices or at home. Most of such methods rely on what are known as "specific binding" reactions in which an unknown substance to be detected (known as a "ligand") reacts specifically and preferentially with a corresponding "receptor" molecule. Most well known specific binding reactions occur between immunoreactants such as antibodies and antigens (substances which produce an immunological response, that is the production of antibodies), but other specific binding reactions (such as between a sugar and lectin, avidin with biotin or hybridization of complementary nucleic acids) are also well known.

Methods in the art using specific binding reactions generally require that one or more or both of the reactants be immobilized on a solid substrate of some type so that unreacted (and generally water-soluble) reactants can be separated from the water-insoluble reaction product (often called a "complex"). In addition, such immobilized reactants can be used in affinity chromatography to remove a desired ligand from a mixture of biologically active materials.

Receptor molecules have thus been immobilized to advantage on particulate substrates such as polymeric particles, glass beads, animal and human erythrocytes, bacterial cells and other solid particles of various sizes. For example, carrier particles prepared from polymers having various surface reactive groups, such as epoxy, carboxy, amino, hydroxy and aldehyde, are described in U.S. Pat. Nos. 4,401,765 (Craig et al) and 4,480,042 (Craig et al).

Biologically active latex particles are described in U.S. Pat. No. 4,563,431 (Pauly et al) as having surface acetal groups which are converted to aldehyde groups for attachment of biologically active substances. The outer polymers are prepared from monomers having pendant acetals linked to the vinyl portion through amidoalkyl groups of 2–7 carbon atoms. The polymers described therein tend to be hydrophilic which is not best for preparing biological reagents because they may have considerable water solubility and thus not be useful as solid substrates in immunoassays.

Other fine particulate carriers are described in U.S. Pat. No. 4,552,633 (Kumakura et al) as having surface aldehyde groups provided by vinyl monomers such as croton aldehyde, acrolein, methacrolein and citral. These monomers are disadvantageous because they lack sufficient hydrophobicity such as that provided by styrene-type monomers. Being hydrophilic, the monomers described by Kumakura et al are unstable for long term storage in aqueous media.

There remains a need in the art to provide biologically active reagents which can be prepared quickly and conveniently and which are colloidally stable under various conditions of use.

Previous aldehyde monomers suffer from the problem of water-solubility and when polymerized, especially using emulsion polymerization techniques, they form water soluble homopolymers and copolymers which contaminate the aqueous phase of the latex. Additionally, such hydrophilic monomers will not readily copolymerize with desired hydrophobic monomers such as styrene and styrene derivatives.

SUMMARY OF THE INVENTION

The problems noted above are overcome with a biologically active reagent comprising:

(I) a water-insoluble particle which is non-swellable in water, and whose outer surface is composed of a polymer derived from an ethylenically unsaturated polymerizable monomer having a pendant aldehyde group and represented by the structure:

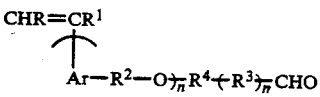

wherein Ar is arylene, R and $R^1$ are independently hydrogen, halo or lower alkyl, $R^2$ and $R^3$ are independently alkylene of 1 to 4 carbon atoms in the chain, $R^4$ is arylene, m is 0 or 1, and n is an integer of 1 to 4, and (II) a biologically active substance covalently attached to the particle through the pendant aldehyde group.

This invention also provides an analytical element comprising a fluid-permeable substrate having one or more reaction zones therein, and containing a biologically active reagent as described above in at least one of the reaction zones.

Moreover, a method for the determination of a specific binding ligand comprises:

A. forming a water-insoluble specific binding complex of a specific binding ligand of interest, or a receptor therefor, with a reagent as described above wherein the biologically active substance is specifically reactive with either the ligand or a receptor therefor, and B. detecting the presence of the complex as an indication of the presence or amount of the ligand.

An analytical separation method comprises:

A. passing a specimen containing a mixture of biologically active substances over an affinity chromatography reagent wherein the reagent is as described above, and the specific binding substance being specific to one or more predetermined biologically active substances in the specimen mixture of biologically active substances to form a complex of the reagent with the predetermined biologically active substances, and B. collecting either the one or more complexed predetermined substances or one or more substances remaining in the eluent.

The invention also provides a method for the detection of a nucleic acid comprising:
A. forming a water-insoluble hybridization product between a nucleic acid of interest and a reagent as described above wherein the biologically active substance is an oligonucleotide which is complementary to the nucleic acid of interest, and
B. detecting the hybridization product as a determination of the nucleic acid of interest.

A kit comprises, separately packaged:
(a) the biologically active reagent as described above having a specific binding material which is useful in the determination of a specific binding species of interest, and
(b) one or more water-soluble reagents useful for the determination of the specific binding species.

The present invention provides reagents which are useful in a variety of analytical, diagnostic and purification methods. These reagents are prepared from polymers which have functional groups readily available for reaction with proteins, nucleic acids and other biological materials of interest. Such attachment can be achieved in a manner which preserves the integrity of the attached material, and utilizes relatively low temperature and milder operating conditions (such as pH). The resulting reagents are colloidally stable even in the absence of surfactants or other dispersing agents in solution and in coated formulations. Other advantages include surprising storage stability in aqueous media having a pH of 5 or less.

The advantages of this invention are provided by preparing reagents from water-insoluble particles prepared from polymerizable monomers having pendant aromatic aldehyde groups as defined herein.

DETAILED DESCRIPTION OF THE INVENTION

The polymers useful in the practice of this invention are homo- or copolymers prepared from one or more ethylenically unsaturated polymerizable monomers having a pendant aldehyde group and represented by the structure:

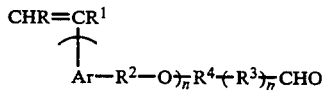

wherein Ar is substituted or unsubstituted arylene of 6 to 14 carbon atoms in the aromatic nucleus (such as phenylene, naphthylene, xylylene and tolylene. Preferably, Ar is substituted or unsubstituted phenylene. Ar can be substituted with one more alkyl groups of 1 to 6 carbon atoms (such as methyl, ethyl, isopropyl, t-butyl, pentyl and hexyl). Preferably, it is unsubstituted. $R^2$ can be attached to Ar in the ortho, meta or para position with the para position being preferred.

R and $R^1$ are independently hydrogen, halo (such as fluoro, chloro or bromo) or substituted or unsubstituted lower alkyl of 1 to 4 carbon atoms (such as methyl, ethyl, isopropyl or n-butyl). Preferably, R is hydrogen and $R^1$ is hydrogen or methyl.

$R^2$ and $R^3$ are independently substituted or unsubstituted alkylene of 1 to 4 carbon atoms in the chain (such as methylene, ethylene, trimethylene, isopropylene, n-butylene, and t-butylene). Preferably, $R^2$ is methylene.

$R^4$ is substituted or unsubstituted arylene of 6 to 14 carbon atoms in the aromatic backbone (defined like Ar above). Preferably, $R^4$ is substituted or unsubstituted phenylene.

In the structure above, m is 0 or 1, and preferably, it is 0. Also, n is 1, 2, 3 or 4, and preferable, it is 1.

Particularly useful monomers include o-, p-or m-formylphenyl vinylbenzyl ether, o-, p- or m-(2-formylethyl)phenyl vinylbenzyl ether, 2-, 3- or 4-formylnaphthyl vinylbenzyl ether, (3- or 4-formyl-2-methylphenyl) vinylbenzyl ether, formylbiphenylyl vinylbenzyl ether and 4 {4-[4-(4-formylphenoxymethyl)phenoxymethyl]phenoxymethyl}styrene The monomers described above can be copolymerized with one or more other ethylenically unsaturated polymerizable monomers to provide useful copolymers. More particularly, the copolymers generally having recurring units derived from:
(a) about 1 to about 100 weight percent of one or more ethylenically unsaturated polymerizable monomers represented by the structure noted above,
(b) 0 to about 99 weight percent of one or more hydrophobic ethylenically unsaturated polymerizable monomers other than those defined in component (a), and
(c) 0 to about 20 weight percent of one or more ethylenically unsaturated polymerizable monomers other than those defined in components (a) and (b).

Preferably, the polymer is composed of from about 2 to about 20 weight percent of component (a), from about 70 to about 98 weight percent of component (b), and from 0 to about 10 weight percent of component (c).

Useful monomers for component (b) noted above include, but are not limited to, ethylenically unsaturated polymerizable oleophilic monomers which provide desired additional hydrophobicity to the copolymers, such as vinyl aromatics (for example, styrene and styrene derivatives such as 4-vinyltoluene, α-methylstyrene, 2,5-dimethylstyrene, 4-t-butylstyrene and 2-chlorostyrene), acrylic and methacrylic acid esters and amides (for example, methyl acrylate, methyl methacrylate, n-butyl acrylate, 2-ethylhexyl methacrylate, benzyl acrylate and N-phenylacrylamide), butadiene, acrylonitrile, vinyl acetate, vinylbenzyl acetate, vinyl bromide, vinylidene chloride and crosslinkable monomers having two or more polymerizable groups. Useful crosslinkable monomers include, but are not limited to divinylbenzene, allyl acrylate and di- and triacrylates and methacrylates (for example 2,2-dimethyl-1,3-propylene diacrylate, 1,4-cyclohexylenedimethylene dimethacrylate, ethylidyne trimethacrylate, ethylene diacrylate, ethylene dimethacrylate, propylene diacrylate and propylene dimethacrylate) and others readily apparent to one skilled in polymer chemistry. A mixture of monomers can be used if desired. Preferred monomers are the vinyl aromatic and crosslinkable monomers.

Monomers useful for component (c) include those which are more hydrophilic in nature, such as monomers having negative or positive charges (as salts or free acids), and nonionic polar monomers. Representative examples of the charged monomers include, but are not limited to, sulfonates, sulfates or carboxylates such as sodium 2-acrylamido-2-methylpropanesulfonate and sodium 3-acryloyloxypropanesulfonate. Representative nonionic polar monomers include, but are not limited to, hydroxyalkyl acrylates and methacrylates (for example, 2-hydroxyethyl acrylate, 2,3-dihydroxypropyl acrylate and 2-hydroxyethyl methacrylate), and acrylamides and methacrylamides (for example, acrylamide, N-isopropylacrylamide, methacrylamide and N-isobutylacrylamide).

The polymers of this invention are prepared using standard emulsion or suspension polymerization techniques, as described for example by Sorenson et al in *Preparative Methods of Polymer Science*, 2nd Ed. (1968), Wiley and Sons, New York, and Stevens, *Polymer Chemistry, An Introduction*, Addison Wesley Publishing Co., London, 1975, and certain preferred conditions are described below in Example 1. Preferably, the polymers are prepared using continuous emulsion polymerization in the absence of surfactants, emulsifiers or colloidal stabilizing agents.

The reagents of this invention have one or more biologically active substances covalently attached to the polymeric particles through the reactive groups (that is, the pendant aldehyde groups) on the outer surface of the particles. As used herein, the term "biologically active substance" is meant to include any organic compound which is found in a living organism or which is useful in the diagnosis, treatment or genetic engineering of cellular material or living organisms, and which has a capacity for interaction with another biological or chemical material. Such substances may or may not be naturally occurring in biological fluids. Such materials must be capable of attaching to the particles through direct or indirect reaction with the reactive groups on the particles. Many such attachment procedures are well known.

Depending upon the intended use of the reagent, the biologically active substances can be from a wide variety of naturally occurring or synthetically prepared materials, including, but not limited to amines, amino acids, peptides, polypeptides, proteins (including hormones, enzymes, lipoproteins, glycoproteins, antibodies, C-reactive protein, serum proteins, and avidin and its derivatives), drugs (for example digoxin, phenytoin, phenobarbital, gentamicin, carbamazepine and theophylline), vitamins (such as biotin and equivalent derivatives), polysaccharides, lipids (including glycolipids), alkaloids, microorganisms, viruses, protozoa, fungi, parasites, rickettsia, molds, blood components, haptens, tissue and organ components, pharmaceuticals, lectins, toxins, nucleic acids (including oligonucleotides, either single- or double-stranded), and components of any of the materials just listed and others known to one skilled in the art.

Particularly useful reagents of this invention are those in which the biologically active substance is a receptor molecule specific to a ligand of interest. Thus, a specific binding reaction involving the reagent can be used for various methods (described in more detail below). Examples of ligand-receptor complexes (that is, reaction of the ligand and receptor) include, but are not limited to antibody-antigen, antibody-hapten, avidin-biotin, sugar-lectin, gelatin-fibronectin and Protein A-IgG complexes. For purposes of this invention, complementary nucleic acids (that is, a hybridized product of complementary strands) are also considered specific binding materials. Such complementary nucleic acids (including oligonucleotides having at least 2 bases) need not be complementary at every base pair, nor must there be a matching base at every position in the nucleic acid sequence. That is, one of the strands can be longer than the other, or one strand can be hybridized with a plurality of oligonucleotides complementary thereto at different sequences.

Most useful biologically active substances are what are known in the art as immunological species which include: (1) any substance which, when presented to an immunocompetent host, will result in the production of a specific antibody capable of binding with that substance, or (2) the antibody so produced, which compound participates in an antigen-antibody reaction. Thus, the immunological species can be an antigenic material or an antibody (including anti-antibodies). Both monoclonal and polyclonal antibodies are useful, and they can be whole molecules or various fragments thereof, as long as they have at least one reactive site for reaction with the reactive groups on the particles, or with linking groups attached or attachable thereto (described below).

If desired, the biologically active substance can be modified or chemically altered to provide reactive groups for attachment including providing a linking moiety for attachment. There is considerable technology known in the art for such chemical modification or the use of linking moieties, including teaching in such references as U.S. Pat. No. 4,914,210 (issued Apr. 13, 1990 to Levenson et al) and WO-A-89/2932 published Apr. 6, 1989) both directed to modification of oligonucleotides, U.S. Pat. No. 4,719,182 (issued Jan. 12, 1988 to Burdick et al), Erlanger et al, *J.Biol.Chem.*, 234, 1090 (1959), Weston et al, *Biochim.Biophys.Acta*, 612, pp.40–49 (1980) and Borzini et al, *J.Immunol.Methods*, 44, pp. 323-332 (1981).

The general procedure for preparing the reagent of this invention is as follows: the polymer particles are mixed with the biologically active substance in an aqueous buffered solution (pH generally from about 5.5 to about 8.5). The % solids of particles is generally from about 0.01 to about 10%, and preferably from about 0.1 to about 3%. The amount of biologically active substance is generally at least about $1 \times 10^{-4}$ weight percent, with from about 0.001 to about 0.1 weight percent being preferred.

Mixing of substance and particles is carried out at a temperature of from about 20 to about 37° C. for from about 2 to about 30 hours. The length of time will vary with the temperature, particular reactive groups on the particles, particular biologically active substance and the desired coverage. Any suitable buffer can be used, but phosphate, 2-(N-morpholino)ethanesulfonic acid and N-(2-hydroxyethyl)-piperazine-N'-3-propanesulfonic acid are preferred. The details of a representative procedure for making a reagent are shown in Example 1 below.

In the analytical or diagnostic methods of this invention, the reagents can be used to detect any specific binding ligand for which there is a receptor molecule. The biologically active substance in a reagent of this invention can be specifically reactive with either the ligand or its receptor. Ligand detection can be carried out in solution or dry form (described below) using test specimens of aqueous fluids (such as biological fluids), or solutions of tissue or cellular materials, and can be quantitative, qualitative or both. In particular, the invention can be used to assay biological fluids of animals, humans or plants, but preferably fluids of humans including whole blood, sera, plasma, lymph, bile, urine, spinal fluid, sputum, lacrimal fluid, dental plaque, perspiration, stool secretions, cellular fluids, tissue cultures, swab specimens, vaginal secretions and semen. It is also possible to assay fluid preparations of human or animal tissue such as skeletal muscle, heart, kidney, lungs, brains, bone marrow or skin.

In general, a method for the determination of a specific binding ligand comprises:

A. forming a water-insoluble specific binding complex of a specific binding ligand of interest, or a receptor therefor, with a reagent comprising:
- (I) a water-insoluble, nonporous particle as described above, and
- (II) a biologically active substance covalently attached to the particle through the pendant aldehyde group, the substance being specifically reactive with either the ligand or with a receptor therefor, and B. detecting the presence of the complex as an indication of the presence or amount of the ligand.

In one embodiment, the reagent can be used in competitive binding assays for determination of a water-soluble, specific binding ligand. The ligand is complexed with a water-soluble receptor for the ligand, and the reagent of this invention. A solution assay is one in which the reagents are included in a suspension of the reagent and test specimen suspected of containing the ligand of interest. Either bound (that is, complexed) or unbound (that is, uncomplexed) materials can be determined in the assay. Physical separation of bound and unbound materials, if desired, can be carried out using any suitable separation technique. In using analytical elements (described below), either vertical or horizontal separation can be used. Bound ligand can be determined using light scattering, turbidimetric, radiometric or spectrophotometric techniques as are known in the art.

In a competitive binding assay, the reagent is generally present in a concentration which depends upon the amount of immunological species (that is, receptor) on the polymeric particles and the ligand of interest. A ligand analog (ligand which is detectably labeled) is also used so there is a competition between ligand and ligand analog for a known amount of receptor available for reaction. The assay is generally carried out by physically contacting and mixing the reagent, ligand analog and test specimen in a suitable container so that complexation occurs. Incubation may be used to promote complexation and any chemical or biological reactions (such as dye formation) needed for detection of either of the complexes.

More particularly, the ligand is an immunological species and the reaction of ligand and receptor therefor forms an immunological complex which is detectable once water-soluble (uncomplexed) materials are removed from the complex (for example, by filtration or centrifugation) to indicate the presence or absence of the species in the specimen.

The methods of this invention can also be carried out using dry analytical elements. The simplest element can be composed of a substrate (preferably absorbent or fluid permeable), for example, a thin sheet of a self-supporting absorbent or bibulous material such as a filter paper or paper strip. This substrate has one or more reaction zones for chemical, biological or specific binding reactions to occur therein. The reagent of this invention is present in at least one of these zones. Other optional zones can include other reagents, such as dyes, dye-providing compounds, scavengers, antioxidants, enzyme substrates or buffers and other materials readily apparent to one skilled in the art. Such elements are known in the art as test strips, analytical elements, slides or dip sticks.

Absorbent materials useful in preparing the elements can include cellulosic materials (such as porous papers), porous polymeric films, mats of glass fibers, woven or nonwoven fabrics and other materials known to one skilled in the art. Preferred substrates are porous spreading layers as described, for example, in U.S. Pat. Nos. 3,992,158 (Przybylowicz et al), 4,258,001 (Pierce et al), 4,292,272 (Kitajima et al) and 4,430,436 (Koyama et al).

Preferred elements can include one or more superposed fluid-permeable layers, all of which are superposed on a nonporous, fluid impermeable support (which can be transparent or not) composed of a suitable polymeric, cellulosic or metallic material. The layers can be used for various purposes, such as for reaction zones, subbing zones, reagent zones, barrier zones, radiation-blocking zones and other uses well known in the art. Where desired, reagents and buffers can move among the layers for the desired reactions to carry out the assay and provide a detectable product and separation of bound and unbound materials. Other components of analytical layers are described, for example, in U.S. Pat. Nos. 4,042,335 (Clement), 4,132,528 (Eikenberry et al), 4,144,306 (Figueras), 4,670,381 (Frickey et al) and EP-A-0 253 581 (published Jan. 2, 1988).

While it is preferred that the reagent of this invention be incorporated into an element for use, this is not critical because the reagent can be added to the element at the time of the assay along with the test specimen. Preferably, however, the ligand analog and reagent of this invention (containing the appropriate receptor) are located within the element in different zones so they will not complex prematurely.

In one preferred embodiment of this invention, an analytical element comprises a nonporous support, having disposed thereon, in order and in fluid contact,
- a reagent layer containing one or more reagents for providing a detectable signal in the assay, and
- a porous spreading layer,
  the element further containing, in one or more layers, the reagent of this invention composed of a receptor (for example, an antibody) for the ligand of interest. A detectably labeled analog of the ligand can be located in a layer other than that containing the reagent of this invention.

Preferably, the ligand analog is labeled with an enzyme, such as one described below, the ligand is an antigenic material, hormone, hapten or drug, and the receptor is the corresponding antibody.

A variety of different elements, depending upon the method of assay, can be prepared according to this invention. They can be configured in a variety of forms, including elongated tapes of any desired width, sheets, slides or chips.

The solution or dry assay of this invention can be manual or automated. In general, in the use of dry elements, analyte determination is made by taking the element from a supply roll, chip packet or other source and physically contacting it with a sample of test specimen so the specimen and reagents within the element become mixed in one or more test zones. Such contact can be accomplished in any suitable manner, for example, by dipping or immersing the element into the sample or, preferably, by applying a drop of the specimen to the element with a suitable dispensing means.

Assay results are generally determined by observing detectable spectrophotometric changes in the element either visually or with suitable detection equipment.

Another embodiment of this invention is what is known in the art as agglutination assays whereby a ligand is complexed with the reagent of this invention to form a detectable agglutination or clumping of the particles. The resulting agglutination can be detected in a variety of ways, for example visually or with suitable light scattering detection equipment. Representative agglutination techniques are described, for example, in U.S. Pat. Nos. 4,419,453 (Dorman et al), 4,808,524 (Snyder et al), 4,828,978 (Warren III et al) and 4,847,199 (Snyder et al).

Agglutination assays are preferably carried out using reagents of the present invention which are detectably labeled in some manner, such as with a radioisotope in the particle or in the biologically active substance attached thereto, or with a colorimetric or fluorometric dye associated with the particle. Most preferably, a dye is within the interior of the particle, that is away from its surface so as to not interfere with the attachment of a biologically active substance or its complexation. Such particles can be core-shell particles having the dye within a core polymer while the shell copolymer is free of dye. This feature and methods of making such particles are described in more detail in U.S. Pat. No. 4,808,524 (noted above) and in EP-A-0 280 556 (published Sep. 12, 1990). In core-shell polymer particles, the shell copolymer has a composition like that described herein (that is, with the necessary pendant aldehyde groups), but the core polymer can be different and need not have such groups.

A method for the determination of an immunological species comprises:

A. contacting a specimen suspected of containing an immunological species with a reagent of this invention having a receptor for the species, to form a water-insoluble immunological complex of the species with the receptor, and B. after separating uncomplexed materials from the water-insoluble complex, detecting the presence of the water-insoluble complex as an indication of the presence or amount of the immunological species in the specimen.

The immunological species can be an antigenic material and the receptor an antibody therefor. Alternatively, the immunological species can be an antibody and the receptor an antigenic material specific therefor. Still again, the immunological species can be an antibody and the receptor an antibody specific therefor.

In still another embodiment, the reagent of this invention can be used in immunometric assays (often called "sandwich" assays). In such assays, the ligand of interest is complexed with two or more receptor molecules (the same or different), one of which is insolubilized or capable of being insolubilized (such as through an avidin-biotin bond), and the other being water-soluble and appropriately labeled (such as with a radioisotope, enzyme, chemiluminescent moiety or other marker known in the art). For example, a sandwich assay for a ligand such as human chorionic gonadotropin (hCG) can be carried out with a reagent of this invention having antibodies to the hormone in combination with enzyme-labeled antibodies to hCG which will complex at different epitopic sites than the reagent antibodies. The resulting sandwich complex is insoluble, detectable and separatable from uncomplexed materials (such as with a microporous membrane). In a preferred embodiment, the reagent of this invention has a receptor for the ligand of interest and is immobilized on the membrane. Sandwich assays are well known in the art, including GB-A-2,074,727 (published Nov. 4, 1981) and U.S. Pat. No. 4,486,530 (David et al), and references noted therein.

Preferably, in the sandwich assays, either prior to, simultaneously with or subsequently to the formation of the water-insoluble complex with the reagent of this invention, the ligand of interest is reacted with a water-soluble specific binding component specifically reactive therefor.

In one embodiment of the sandwich assay, the reagent of this invention is directly reacted with the ligand of interest, for example, where the ligand is an antigen, and the reagent has antibodies thereto. In another embodiment, however, the reagent is complexed with the ligand indirectly, that is, through an intermediate linking moiety. One example of this is shown in U.S. Pat. No. 4,870,007 (to Smith-Lewis), where complexation is through an avidin-biotin bond.

Another embodiment of this invention is what is known as a hybridization assay wherein a targeted nucleic acid is detected using complementary probes, one of which is suitably labeled, and the other is immobilized, or capable of being immobilized. The reagent of this invention can be used as an immobilization probe in such assays. Examples of hybridization assays are shown, for example, in U.S. Pat. Nos. 4,358,535 (Falkow et al) and 4,486,539 (Ranki et al). These reagents can also be used as capture probes after what is known in the art as polymerase chain reaction amplification, for example, as described in more detail in U.S. Pat. Nos. 4,683,195 (Mullis et al), 4,683,202 (Mullis) and EP-A-0 370 694 (published Jul. 24, 1991).

The analytical, sandwich and hybridization assays of this invention can be carried out using suitable equipment and procedures whereby complexed or hybridized product is captured or separated from uncomplexed materials by filtration, centrifugation or other means. Preferably, such assays are carried out using disposable test devices which contain microporous filtration membranes (for example those commercially available from Pall Corp.). Representative test devices are shown in U.S. Pat. Nos. 3,825,410 (Bagshawe), 3,970,429 (Updike) and 4,446,232 (Liotta). Particularly useful test devices are shown in U.S. Ser. No. 98,248 (filed Sep. 18, 1987 by Hinckley et al), and are commercially available as Surecell TM test devices (Eastman Kodak Co.). Self-containing pouches are described, for example, in EP-A-0 408 738. In some embodiments, the reagent is disposed on a microporous membrane.

The analytical separation method of this invention can be used to isolate one or more analytes of interest from a mixture of biological materials. Thus, the reagent of this invention (or several reagents having different substances attached to particles) is generally placed in a column through which a fluid containing the mixture of biological materials is poured, allowing the reagent to extract from the fluid those materials one wants to isolate. This may be useful in the purification of nucleic acids, enzymes, carbohydrates, proteins, lipids, vitamins, steroids, antibodies, peptides or hormones. This procedure is also known as affinity chromatography.

Affinity chromatography can also be used to concentrate dilute solutions of proteins in order to remove denatured forms thereof from refined proteins, and in the separation and resolution of protein and peptide components which have originated in specific chemical modifications.

Another use of this method is to purify nucleic acids, such as those resulting from polymerase chain reaction amplification, as described, for example in EP-A-0 388 171 (published Jun. 5, 1991).

The reagent of this invention can be supplied for any of the described methods as a single material, or it can be supplied in an analytical element as described above, or yet again in combination with other reagents, test devices and equipment in a diagnostic test kit. For the purification method, the reagent can also be supplied in an affinity chromatography column.

Specifically, a kit for a hybridization assay includes a reagent of this invention having an oligonucleotide complementary to the nucleic acid of interest, and one or more other reagents (for example, labeled probe or polymerase chain reaction reagents), solutions (such as wash or extraction solutions) or articles (such as pipettes, filters, test devices or test vessels) needed for the assay.

In another embodiment, a kit useful for determination of a ligand (for example immunoassay, sandwich assay, diagnostic test or competitive binding assay) includes the reagent of this invention, and one or more other reagents, solutions or articles needed for such an assay (such as ligand analog, labeled receptor, dye-providing compositions, substrates, wash solutions, filters, test devices, extraction reagents and others known in the art).

In the analytical purification method of this invention, the reagent in the chromatography column captures one or more of the substances in the mixture of substances poured through the column.

In one embodiment, the predetermined substances are captured by the reagent, the original eluent is discarded and the captured substances are removed from the column using a solvent which alters the binding characteristics of the substances so they can be uncomplexed. Such solvents include buffers which alter the pH, salt solutions which alter the ionic nature of the complex or solutions containing a second species which will specifically bind to the reagent and replace the captured substance.

Alternatively, the predetermined substances captured by the reagent are discarded, and other chemical or biological materials remaining in the original eluent are collected.

The following examples are for illustrative purposes only, and not meant to limit the scope of the invention. All percentages are by weight, unless otherwise specified.

EXAMPLE 1

Preparation of Biologically Active Reagent

This example demonstrates the preparation of a reagent of this invention.

To prepare polymeric particles having pendant aldehyde groups, the following three solutions of reagents were pumped, under continuous stirring, into a reaction vessel heated at 80° C. and the noted pumping rates:

Solution 1: Contained styrene (839.4 g), p-formalphenyl vinylbenzyl ether (44.18 g), and dodecanethiol (8.84 g) pumped at 2.5 ml/min.

Solution 2: Contained ammonium persulfate (17.67 g) and distilled water (1661.96 g) pumped at 4 ml/min.

Solution 3: Contained sodium metabisulfite (8.84 g) and distilled water (1661.96 g) pumped at 3.7 ml/min.

After an addition time of 360 minutes, pumping was stopped to provide 1077 g latex having 20.4% solids. No surfactant was used in the preparation of the particles. After dialysis of the resulting latex for seven days against distilled water, the resulting purified latex (pH 5.86) contained 14.8% solids of particles having an average diameter of 1.44 μm.

One portion of the latex containing 30 mg dry weight of polymer particles was mixed with $^3$H bovine gamma globulin (0.2 mg) and brought to a final volume of 1.5 ml with sodium phosphate buffer (0.1 molar, pH 6) in a centrifuge tube. Attachment of the protein to the particles was continued for 24 hours at room temperature by end-over-end rotation at 30–35 rpm while attached to a rotating plate mounted at a 45 degree angle in the capped tube. This was labeled Tube #1.

A second tube (#2) had identical contents except sodium cyanoborohydride (10 nmolar, 150 μl) was added to the tube before the 24 hours of reaction.

Tubes #3 and #4 were similarly prepared to #1 and #2, respectively, except 4-(2-hydroxyethyl)-1-piperazinepropanesulfonic acid (0.1 molar, 1.5 ml) was used in place of phosphate buffer.

After 24 hours of reaction, excess bovine gamma globulin (30 mg, 30 mg/ml in buffer) was added to each tube. The contents were then incubated another 4 hours at room temperature.

The total amount of labeled protein attached to the particles was determined by measuring: (a) the total counts per minute (cpm) in a 500 μl aliquot of the tube contents, (b) the cpm remaining in the supernatant following centrifugation of a 1 ml sample of the tube contents, and (c) the cpm bound to the particles following washing of the pellet obtained in (b).

The fraction of the labeled protein which was covalently bound to the particles was determined following incubation of the reagents in the presence of sodium dodecylsulfate (1%) at 37° C. for about 24 hours with end-over-end rotation. The same procedure described above for determining total bound protein was also used to determine the amount of labeled protein covalently bound. The results are shown in Table I below:

TABLE I

| Tube | % Bound $^3$H—BGG | |
|---|---|---|
| | Total | Covalent |
| 1 | 93.3 | 6 |
| 2 | 95.3 | 57 |
| 3 | 80.9 | 5 |
| 4 | 86.9 | 50 |

These data indicate that the labeled protein was covalently attached in the presence of sodium cyanoborohydride.

EXAMPLE 2

Stability of Reagents

This example demonstrates the improved stability of the reagents of this invention. To demonstrate the stability, the reagent described in Example 1 was evaluated for the amount of $^3$H bovine gamma globulin covalently bound after aging at 4° C. for 7 months. A similar reagent was evaluated immediately after preparation ("fresh", that is, no aging). This reagent was prepared from a 9:1 weight ratio of styrene and p-formalphenyl vinylbenzyl ether.

Using the procedure described above in Example 1, the amount of covalently bound protein was determined to be as shown in the following Table II.

TABLE II

| Reagent | % $^3$H—BGG Covalently Bound |
|---|---|
| Aged | 69 |
| Fresh | 55 |

These data indicate that storage of the reagent did not adversely affect the stability of the reagent. The "aged" reagent also compared favorably with the reagents shown in Table I of Example 1.

EXAMPLE 3

Preparation of Reagent with Antibody

This example illustrates the preparation of a reagent of this invention which is formed from an antibody specific to thyroxine and polymeric particles having pendant aldehyde groups.

One portion of the latex described in Example 1 containing 30 mg dry weight of polymer particles was mixed with a monoclonal antibody specific to thyroxine (0.2 mg, Cambridge Catalog No 200-077M Lot # A5641) and brought to a final volume of 1.5 ml with sodium phosphate buffer (0.1 molar, pH 6) in a centrifuge tube. Attachment of the antibody to the particles was continued for 24 hours at room temperature by end-over-end rotation at 30–35 rpm while attached to a rotating plate mounted at a 45 degree angle in the capped tube. This was labeled Tube #1.

A second tube (#2) had identical contents except sodium cyanoborohydride (10 nmolar, 150 μl) was added to the tube before the 24 hours of reaction.

Tubes #3 and #4 were similarly prepared to #1 and #2, respectively, except 4-(2-hydroxyethyl)-1-piperazinepropanesulfonic acid (0.1 molar, 1.5 ml) was used in place of phosphate buffer.

After 24 hours of reaction, bovine gamma globulin (30 mg, 30 mg/ml in buffer) was added to each tube. The contents were then incubated another 4 hours at room temperature to provide the reagent of this invention.

The invention has been described in detail with particular reference to preferred embodiments thereof, but it will be understood that variations and modifications can be effected within the spirit and scope of the invention. All patents, patent applications (published or unpublished, domestic or foreign), journal literature, books and other published prior art cited herein are incorporated herein by reference for the teaching therein pertinent to this invention.

We claim:

1. A biologically active reagent comprising:
   (I) a water-insoluble particle which is non-swellable in water, and consists essentially of a homopolymer or copolymer derived by emulsion or suspension polymerization from an ethylenically unsaturated polymerizable monomer having a pendant aldehyde group and represented by the structure:

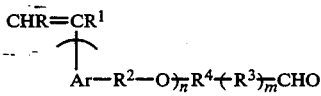

wherein Ar is arylene, R and $R^1$ are independently hydrogen, halo or lower alkyl, $R^2$ and $R^3$ are independently alkylene of 1 to 4 carbon atoms in the chain, $R^4$ is arylene, m is 0 or 1, and n is an integer of 1 to 4, and (II) a biologically active substance covalently attached to said particle through said pendant aldehyde group.

2. The reagent of claim 1 wherein Ar is phenylene, R is hydrogen, $R^1$ is hydrogen or methyl, $R^2$ is methylene, $R^4$ is phenylene, m is 0 and n is 1.

3. The reagent of claim 1 wherein said monomer is selected from the group consisting of o-, p- or m-formylphenyl vinylbenzyl ether, o-, p- or m- (2-formylethylphenyl vinylbenzyl ether, 2-, 3- or 4-formylnaphthyl vinylbenzyl ether, (3- or 4-formyl-2-methylphenyl) vinyl benzyl ether, formylbiphenylyl vinylbenzyl ether and 4-{4-[4 -(4-formylphenoxymethyl)phenoxymethyl]-phenoxymethyl}styrene.

4. The regent of claim 1 wherein said homopolymer or copolymer has recurring units derived from:
   (a) about 1 to about 100 weight percent of one or more ethylenically unsaturated polymerizable monomers represented by the structure:

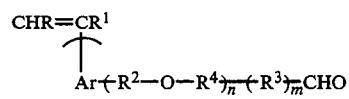

wherein Ar is arylene, R and $R^1$ are independently hydrogen, halo or lower alkyl, $R^2$ and $R^3$ are independently alkylene of 1 to 4 carbon atoms in the chain, $R^4$ is arylene, m is 0 or 1, and n is an integer of 1 or 4,
   (b) 0 to about 99 weight percent of one or more hydrophobic ethylenically unsaturated polymerizable monomers other than those defined in component (a) and which is selected from the group consisting of vinyl aromatics, acrylic and methacrylic esters and amides, butadiene, acrylonitrile, vinyl acetate, vinylbenzyl acetate, vinyl bromide, vinylidene chloride and crosslinkable monomers, and
   (c) 0 to about 20 weight percent of one or more ethylenically unsaturated polymerizable monomers other than those defined in components (a) and (b).

5. The reagent of claim 4 wherein Ar is phenylene, R is hydrogen, $R^1$ is independently hydrogen or methyl, $R^2$ is methylene, $R^4$ is phenylene, m is 0, and n is 1, and said monomers (b) are vinyl aromatic monomers or crosslinkable monomers.

6. The reagent of claim 4 wherein said copolymer is composed of from about 2 to about 20 weight percent of component (a), from about 70 to about 98 weight percent of component (b), and from 0 to about 10 weight percent of component (c).

7. The reagent of claim 1 wherein said biologically active substance is selected from the group consisting of amines, amino acids, peptides, polypeptides, proteins, drugs, steroids, vitamins, polysaccharides, lipids, alkaloids, microorganisms, viruses, protozoa, fungi, parasites, rickettsia, molds, blood components, haptens, organ components, pharmaceuticals, lectins, toxins, nucleic acids, and components of one of the foregoing materials.

8. The reagent of claim 7 wherein said biologically active substance is an antibody or nucleic acid.

9. An analytical element comprising a fluid-permeable substrate having one or more reaction zones therein, and containing in at least one of said reactions zones, a biologically active reagent comprising:
(I) a water-insoluble particle which is non-swellable in water and consists essentially of a homopolymer or copolymer derived by emulsion or suspension polymerization from an ethylenically unsaturated polymerizable having a pendant aldehyde group and represented by the structure:

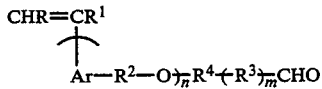

wherein Ar is arylene, R and $R^1$ are independently hydrogen, halo or lower alkyl, $R^2$ and $R^3$ are independently alkylene of 1 to 4 carbon atoms in the chain, $R^4$ is arylene, m is 0 or 1, and n is an integer of 1 to 4, and
(II) a biologically active substance covalently attached to said particle through said pendant aldehyde group.

10. The element of claim 9 wherein said biologically active substance is an antibody.

11. An analytical element comprising a nonporous support, having disposed thereon, in order and in fluid contact,
a reagent layer containing one or more reagents for providing a detectable signal in response to a ligand of interest, and
a porous spreading layer,
said element further containing, in one or more layers, a biologically active reagent comprising:
(I) a water-insoluble particle which is non-swellable in water, and consists essentially of a homopolymer or copolymer derived by emulsion or suspension polymerization from an ethylenically unsaturated poolymerizable monomer having a pendant aldehyde group and represented by the structure:

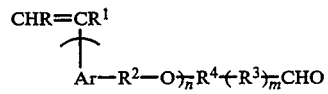

wherein Ar is arylene, R and $R^1$ are independently hydrogen, halo or lower alkyl, $R^2$ and $R^3$ are independently alkylene of 1 to 4 carbon atoms in the chain, $R^4$ is arylene, m is 0 or 1, and n is an integer of 1 to 4, and
(II) a receptor for said ligand covalently attached to said particle through said pendant aldehyde group.

12. The element of claim 11 further comprising a detectably labeled analog of said ligand which is located in a layer other than that containing said biologically active reagent.

13. A method for the determination of a specific binding ligand comprising:
A. forming a water-insoluble specific binding complex of a specific binding ligand of interest, or a receptor therefor, with a reagent comprising:
(I) a water-insoluble particle which is non-swellable in water, and consists essentially of a homopolymer or copolymer derived by emulsion or suspension polymerization from an ethylenically unsaturated polymerizable monomer having a pendant aldehyde group and represent by the structure:

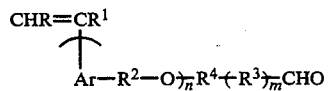

wherein Ar is arylene, R and $R^1$ are independently hydrogen, halo or lower alkyl, $R^2$ and $R^3$ are independently alkylene of 1 to 4 carbon atoms in the chain, $R^4$ is arylene, m is 0 or 1, and n is an integer of 1 to 4, and
(II) a biologically active substance covalently attached to said particle through said pendant aldehyde group, said biologically active substance being specifically reactive with either said ligand or a receptor therefor, and
B. detecting the presence of said complex as an indication of the presence of amount of said ligand.

14. The method of claim 13 wherein said ligand is an antigenic material and said receptor is an antibody specific to said antigenic material or a component thereof.

15. The method of claim 13 wherein said ligand is a single stranded nucleic acid and said receptor is an oligonucleotide complementary to said nucleic acid.

16. The method of claim 13 wherein said ligand is avidin or biotin, and said receptor is biotin or avidin, respectively.

17. A competitive binding assay for the determination of a water-soluble specific binding ligand comprising:
A. contacting a specimen suspected of containing a water-soluble specific binding ligand of interest with both
a water-soluble specific receptor for said ligand, and
a reagent comprising:
(I) a water-insoluble particle which is non-swellable in water, and consists essentially of a homopolymer or copolymer derived by emulsion or suspension polymerization from an ethylenically unsaturated polymerizable monomer having a pendant aldehyde group and represented by the structure:

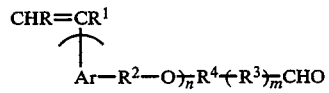

wherein Ar is arylene, R and $R^1$ are independently hydrogen, halo or lower alkyl, $R^2$ and $R^3$ are independently alkylene of 1 to 4 carbon atoms in the chain, $R^4$ is arylene, m is 0 or 1, and n is an integer of 1 to 4, and
(II) molecules of said ligand covalently attached to said particle through said pendant aldehyde group,
to form a water-soluble specific binding complex
(a) between said receptor and said ligand, and a water-insoluble specific binding complex (b) between said receptor and said water-soluble reagent, and
B. after separating complexes (a) and (b), detecting the presence of either complex as a determination of said ligand.

18. A competitive binding assay for the determination of a specific binding ligand comprising:
A. contacting a specimen suspected of containing a water-soluble specific binding ligand of interest with both
  a water-soluble detectable analog of said ligand, and
  a reagent comprising:
    (I) a water-insoluble particle which is non-swellable in water, and consists essentially of a homopolymer or copolymer derived by emulsion or suspension polymerization from an ethylenically unsaturated polymerizable monomer having a pendant aldehyde group and represented by the structure:

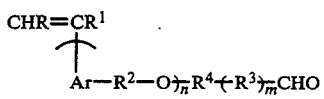

wherein Ar is arylene, R and $R^1$ are independently hydrogen, halo or lower alkyl, $R^2$ and $R^3$ are independently alkylene of 1 to 4 carbon atoms in the chain, $R^4$ is arylene, m is 0 or 1, and n is an integer of 1 to 4, and
    (II) a receptor for said ligand covalently attached to said particle through said pendant aldehyde group,
to form a water-insoluble specific binding complex (a) between said water-insoluble receptor and said ligand, and water-insoluble specific binding complex (b) between said water-insoluble receptor and said ligand analog, and
B. after separating complexes (a) and (b), detecting the presence of either complex as a determination of said ligand.

19. A method for the determination of an immunological species comprising:
A. contacting a specimen suspected of containing an immunological species with a reagent comprising:
    (I) a water-insoluble particle which is non-swellable in water, and consists essentially of a homopolymer or copolymer polymer derived by emulsion or suspension polymerization from an ethylenically unsaturated polymerizable monomer having a pendant aldehyde group and represented by the structure:

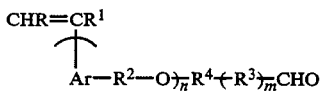

wherein Ar is arylene, R and $R^1$ are independently hydrogen, halo or lower alkyl, $R^2$ and $R^3$ are independently alkylene of 1 to 4 carbon atoms in the chain, $R^4$ is arylene, m is 0 or 1, and n is an integer of 1 to 4, and
    (II) a receptor for said species covalently attached to said particle through said pendant aldehyde group,
to form a water-insoluble immunological complex of said species with said receptor, and
B. after separating uncomplexed materials from said water-insoluble complex, detecting the presence of said water-insoluble complex as an indication of the presence or amount of said immunological species in said specimen.

20. The method of claim 19 for the determination of an antigenic material wherein said receptor is an antibody for said antigenic material.

21. The method of claim 19 for the determination of an antibody wherein said receptor is a second antibody directed to said antibody to be determined.

22. The method of claim 19 for the determination of an antibody wherein said receptor is an antigenic material specific for said antibody.

23. The method of claim 19 wherein said uncomplexed materials are separated from said immunological complex by filtration using a microporous membrane.

24. The method of claim 23 wherein said reagent is disposed on said membrane.

25. The method of claim 19 wherein, either prior to, simultaneously with or subsequently to the formation of said water-insoluble immunological complex, said immunological species is reacted with a water-soluble specific binding component specifically reactive therefor.

26. An analytical separation method comprising:
A. passing a specimen containing a mixture of biologically active substances over an affinity chromatography reagent comprising:
    (I) a water-insoluble particle which is non-swellable in water, and consists essentially of a copolymer or homopolymer derived by emulsion or suspension polymerization from an ethylenically unsaturated polymerizable monomer having a pendant aldehyde group and represented by the structure:

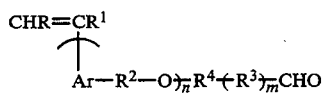

wherein Ar is arylene, R and $R^1$ are independently hydrogen, halo or lower alkyl, $R^2$ and $R^3$ are independently alkylene of 1 to 4 carbon atoms in the chain, $R^4$ is arylene, m is 0 or 1, and n is an integer of 1 to 4, and
    (II) a specific binding substance covalently attached to said particle through said pendant aldehyde group, said specific binding substance being specific to one or more predetermined biologically active substances in said specimen mixture of biologically active substances
to form a complex of said reagent with said predetermined biologically active substances, and
B. collecting either the one or more complexed predetermined substances or one or more substances remaining in the eluent.

27. A method for the detection of a nucleic acid comprising:
A. forming a water-insoluble hybridization product between a nucleic acid of interest and a reagent comprising:
    (I) a water-insoluble particle which is non-swellable in water, and consists essentially of a homopolymer or copolymer polymer derived by emulsion or suspension polymerization from an ethylenically unsaturated polymerizable monomer having a pendant aldehyde group and represented by the structure:

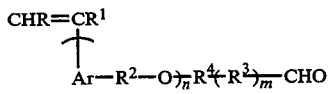

wherein Ar is arylene, R and $R^1$ are independently hydrogen, halo or lower alkyl, $R^2$ and $R^3$ are independently alkylene of 1 to 4 carbon atoms in the chain, $R^4$ is arylene, m is 0 or 1, and n is an integer of 1 to 4, and (II) an oligonucleotide covalently attached to said particle through said pendent aldehyde group, said oligonucleotide being complementary to said nucleic acid of interest, and B. detecting the hybridization product as a determination of said nucleic acid of interest.

28. The method of claim 27 wherein said nucleic acid of interest is amplified using polymerase chain reaction prior to contact with said reagent.

29. A kit comprising, separately packaged:
(a) a biologically active reagent comprising:
(I) a water-insoluble particle which is non-swellable in water, and consists essentially of a homopolymer or copolymer derived by emulsion or suspension polymerization from an ethylenically unsaturated polymerizable monomer having a pendant aldehyde group and represented by the structure:

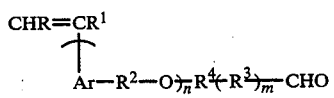

* * * * *